(12) United States Patent
Jang et al.

(10) Patent No.: US 12,419,503 B2
(45) Date of Patent: Sep. 23, 2025

(54) ENDOSCOPE SYSTEM HAVING A THREE-DIMENSIONAL EXPANSION PROCESSOR

(71) Applicant: HOYA CORPORATION, Tokyo (JP)

(72) Inventors: Minsul Jang, Tokyo (JP); Kohei Iketani, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 513 days.

(21) Appl. No.: 17/919,395

(22) PCT Filed: Apr. 26, 2021

(86) PCT No.: PCT/JP2021/016660
§ 371 (c)(1),
(2) Date: Oct. 17, 2022

(87) PCT Pub. No.: WO2021/221017
PCT Pub. Date: Nov. 4, 2021

(65) Prior Publication Data
US 2023/0157526 A1 May 25, 2023

(30) Foreign Application Priority Data
Apr. 28, 2020 (JP) ................................. 2020-079593

(51) Int. Cl.
*A61B 1/00* (2006.01)
*A61B 1/05* (2006.01)
(Continued)

(52) U.S. Cl.
CPC .... *A61B 1/00194* (2022.02); *A61B 1/000094* (2022.02); *A61B 1/000096* (2022.02);
(Continued)

(58) Field of Classification Search
None
See application file for complete search history.

(56) References Cited

U.S. PATENT DOCUMENTS

2006/0268257 A1* 11/2006 Ogawa ............... A61B 1/00048
356/3.13
2007/0161854 A1* 7/2007 Alamaro .............. A61B 1/0676
600/109
(Continued)

FOREIGN PATENT DOCUMENTS

| CN | 105939650 A | 9/2016 |
| CN | 105722450 A | 5/2019 |

(Continued)

OTHER PUBLICATIONS

Notice of Reasons for Refusal issued in Japanese Counterpart Patent Appl. No. 2022-518057, dated Nov. 22, 2022.
(Continued)

*Primary Examiner* — John P Leubecker
(74) *Attorney, Agent, or Firm* — GREENBLUM & BERNSTEIN, P.L.C.

(57) ABSTRACT

An endoscope system includes an endoscope that captures a living tissue in a body cavity, and an image processing unit. The endoscope includes an objective lens provided on a front side of a light receiving surface of an image sensor and configured to simultaneously form images of the living tissue, obtained through a plurality of windows, on the light receiving surface as the captured image. The image processing unit includes a three-dimensional expansion processor configured to calculate different directions of a feature part visible through the plurality of windows based on position information in each of images of the feature part, which is distinguishably identified from other parts and included in common in the plurality of images obtained through the plurality of windows in the captured image captured by the endoscope, and to expand two-dimensional information of the images of the feature part to three-dimensional information.

7 Claims, 13 Drawing Sheets

(51) Int. Cl.
    *G06V 10/56*     (2022.01)
    *H04N 13/207*     (2018.01)

(52) U.S. Cl.
    CPC ...... *A61B 1/00045* (2013.01); *A61B 1/00096* (2013.01); *A61B 1/00193* (2013.01); *A61B 1/05* (2013.01); *G06V 10/56* (2022.01); *H04N 13/207* (2018.05)

(56) References Cited

U.S. PATENT DOCUMENTS

| | | | |
|---|---|---|---|
| 2014/0152802 | A1 | 6/2014 | Olsson et al. |
| 2015/0062299 | A1* | 3/2015 | Brown ................. H04N 13/239 348/45 |
| 2016/0242627 | A1 | 8/2016 | Takahashi |
| 2016/0338575 | A1 | 11/2016 | Honda et al. |
| 2018/0092515 | A1* | 4/2018 | Yashiro ............. A61B 1/00181 |
| 2018/0214006 | A1 | 8/2018 | Akimoto et al. |
| 2018/0276877 | A1 | 9/2018 | Mountney et al. |
| 2018/0353053 | A1 | 12/2018 | Fukushima |
| 2019/0034029 | A1* | 1/2019 | Huang ................. G06F 3/0418 |
| 2019/0186287 | A1* | 6/2019 | Lowery .................... H05H 1/46 |
| 2019/0188842 | A1* | 6/2019 | Sakamoto ................. G06T 7/62 |
| 2019/0365252 | A1* | 12/2019 | Fernald ................. A61B 5/004 |
| 2020/0053296 | A1* | 2/2020 | Endo ....................... H04N 23/60 |
| 2020/0107886 | A1 | 4/2020 | Govari et al. |
| 2020/0294234 | A1* | 9/2020 | Rance .................... G06F 18/22 |
| 2021/0056695 | A1 | 2/2021 | Mori |

FOREIGN PATENT DOCUMENTS

| | | |
|---|---|---|
| EP | 3130273 B1 | 5/2019 |
| JP | 2012170774 A | 9/2012 |
| JP | 2018-57799 A | 4/2018 |
| JP | 2020-512089 A | 4/2020 |
| WO | 2017/145270 A1 | 8/2017 |
| WO | 2019/244345 A1 | 12/2019 |

OTHER PUBLICATIONS

Office Action issued in Chinese related Patent Appl. No. 202180019989, dated Oct. 31, 2024.
Search Report issued in EPO Counterpart Patent Appl. No. 21797476.5, dated Apr. 10, 2024.
International Search Report issued in International Bureau of WIPO Patent Application No. PCT/JP2021/016660, dated Jun. 29, 2021, along with an English translation thereof.

* cited by examiner

ENDOSCOPE SYSTEM HAVING A THREE-DIMENSIONAL EXPANSION PROCESSOR

TECHNICAL FIELD

The present invention relates to an endoscope system that captures a living tissue in a body cavity.

BACKGROUND ART

An endoscope is a device that includes an image sensor inserted into a body cavity of a human body or the like and capturing a living tissue on an inner surface of the body cavity. The endoscope is inserted into, for example, the large intestine, and displays a captured image on a monitor in order to determine the presence or absence of an unhealthy site, for example, the presence or absence of a lesion site, in the living tissue. When the living tissue in the large intestine is diagnosed, it is necessary to determine whether or not there is a lesion site on a base part of a fold by pushing the fold down in one direction while pulling the endoscope in one direction so that the fold protruding from the inner surface of the body cavity does not interfere with the capturing. However, a lesion site may be present on a portion hidden in a shadow of the fold even when the fold is pushed down in one direction. Further, when a visual field of an image to be captured is narrow, it is difficult to capture a portion between adjacent folds is some cases.

Therefore, in order to capture the portion between the folds before pushing the fold down, an objective lens having a wide viewing angle may be used for an objective optical system of the image sensor.

For example, there is known an endoscope system including: an endoscope that includes an insertion portion to be inserted into an observation target, a front-view observation unit having a visual field in a direction of a distal tip of the insertion portion, a side-view observation unit having a visual field in a direction of a side surface of the insertion portion, and a protrusion protruding from the insertion portion and forming a blind spot in the visual field of the side-view observation unit; and an image acquisition unit that acquires a front-view observation image using the front-view observation unit and acquires a side-view observation image using the side-view observation unit (see JP 2018-57799 A).

SUMMARY OF INVENTION

Technical Problem

In the endoscope system, the front-view observation image and the side-view observation image can be simultaneously acquired, and a wide range of the observation target can be simultaneously displayed on a display unit. However, the front-view observation image and the side-view observation image are two-dimensional images, and thus, when captured images are displayed, it is difficult for an operator of the endoscope to know information on surface unevenness of a lesion site from the displayed captured images. Obtaining the information on surface unevenness in addition to a size of the lesion site is important for diagnosing the degree of progression of the lesion site.

Therefore, an object of the present invention is to provide an endoscope system capable of obtaining three-dimensional information of a feature part such as a lesion site using a captured image when a living tissue is captured.

Solution to Problem

One aspect of the present invention is an endoscope system including: an endoscope that captures a living tissue in a body cavity; and an image processing unit that performs image processing on a captured image captured by the endoscope.

The endoscope includes:
an image sensor configured to capture an image of the living tissue; and
an objective lens provided on a front side of a light receiving surface of the image sensor and configured to form the image of the living tissue on the light receiving surface, and
the image processing unit includes
a three-dimensional expansion processor configured to calculate different directions of a feature part visible from at least two different capturing positions based on position information of the feature part, which is distinguishably identified from other parts and included in common in a plurality of the captured images captured at the different capturing positions by the endoscope, and to expand two-dimensional information of an image of the feature part to three-dimensional information.

Preferably, the capturing positions are different positions obtained by moving the endoscope with respect to the living tissue, and
the three-dimensional expansion processor calculates the three-dimensional information by using the different directions of the feature part visible from the different capturing positions and distance information between the capturing positions.

Another aspect of the present invention is also an endoscope system including: an endoscope that captures a living tissue in a body cavity; and an image processing unit that performs image processing on a captured image captured by the endoscope.

The endoscope includes:
an image sensor configured to capture an image of the living tissue; and
an objective lens provided on a front side of a light receiving surface of the image sensor and configured to simultaneously form a plurality of the images of the living tissue, obtained through a plurality of windows, on the light receiving surface as the captured image, and
the image processing unit includes
a three-dimensional expansion processor configured to calculate different directions of a feature part visible through the plurality of windows based on position information in each of images of the feature part, which is distinguishably identified from other parts and included in common in the plurality of images obtained through the plurality of windows in the captured image captured by the endoscope, and to expand two-dimensional information of the feature part to three-dimensional information.

Preferably, the plurality of windows include a front window facing the front side of the light receiving surface of the image sensor and a side window facing a lateral side as compared with the front window,
the objective lens is configured to simultaneously form a front-view image of the living tissue obtained through the front window and a side-view image of the living tissue obtained through the side window on the light receiving surface as the captured image, and the three-dimensional expansion processor is configured to expand the two-dimensional information to the three-dimensional information by calculating different directions of the feature part visible through the front window and the side window based on position information of the feature part in the front-view image and position information of the feature part in the side-view image, the feature part being included in common in the front-view image and the side-view image in the captured image captured by the endoscope.

Preferably, the plurality of images include an image of an overlapping area including the identical part of the living tissue as the image, and the position information in each of the images of the feature part is information obtained when the feature part is located in the overlapping area.

Preferably, the image sensor continuously captures the living tissue, and the plurality of images including the feature part are captured images having mutually different capturing positions before and after the endoscope is moved in the body cavity.

Preferably, the image processing unit includes an identity determination section configured to determine whether or not the feature part included in each of the plurality of images is identical using at least one of color information and an outline shape information of the feature part.

Preferably, the three-dimensional expansion processor includes a predictive model that performs machine learning of a relationship between the two-dimensional information and the three-dimensional information using the two-dimensional information and the three-dimensional information of the image of the feature part in a plurality of the captured images including the feature part of the living tissue captured by the endoscope as training data, and is configured to acquire the three-dimensional information by inputting the two-dimensional information of the captured image captured by the endoscope to the predictive model.

Another aspect of the present invention is also an endoscope system including: an endoscope that captures a living tissue in a body cavity; and an image processing unit that performs image processing on a captured image captured by the endoscope.

The endoscope includes an image sensor configured to capture an image of the living tissue, and an objective lens provided on a front side of a light receiving surface of the image sensor and configured to form the image of the living tissue on the light receiving surface, and the image processing unit includes a prediction section including a predictive model configured to input two-dimensional information of a feature part, that is included in the captured image captured by the endoscope and is distinguishably identified from other parts, to predict three-dimensional information from the two-dimensional information.

The predictive model is a model obtained by using a plurality of the captured images, which are already known and include the feature part, as training data and performing machine learning of a relationship between the two-dimensional information of the feature part that is known and the three-dimensional information of the feature part that is known in the captured image.

Preferably, the endoscope system further includes a monitor configured to display an image using the three-dimensional information obtained by the prediction section, the image sensor is configured to simultaneously capture images obtained through a plurality of windows, the image sensor continuously captures the living tissue, a visual field range of the image sensor includes a blind spot area in which a part of the living tissue is not captured through any of the plurality of windows, and the image processing unit includes an image display control section that performs control to display a three-dimensional image of a whole of the feature part on the monitor using the three-dimensional information predicted from the two-dimensional information of the feature part before at least a part of the feature part is located in the blind spot area when the at least part of the feature part is located in the blind spot area.

Preferably, the endoscope system further includes a monitor configured to display an image using the three-dimensional information obtained by the prediction section, the image sensor is configured to simultaneously capture images obtained through a plurality of windows, the image sensor continuously captures the living tissue, a visual field range of the image sensor includes an overlapping area that is simultaneously captured through the plurality of windows, and the image processing unit includes an image display control section that performs control to display one three-dimensional image of a whole of the feature part on the monitor using the three-dimensional information predicted from the two-dimensional information of the feature part before at least a part of the feature part is located in the overlapping area when the at least part of the feature part is located in the overlapping area.

Advantageous Effects of Invention

According to the above-described endoscope system, when the living tissue is captured, the three-dimensional information of, the feature part such as the lesion site can be obtained using the captured image.

DESCRIPTION OF EMBODIMENTS

Figure 1A:
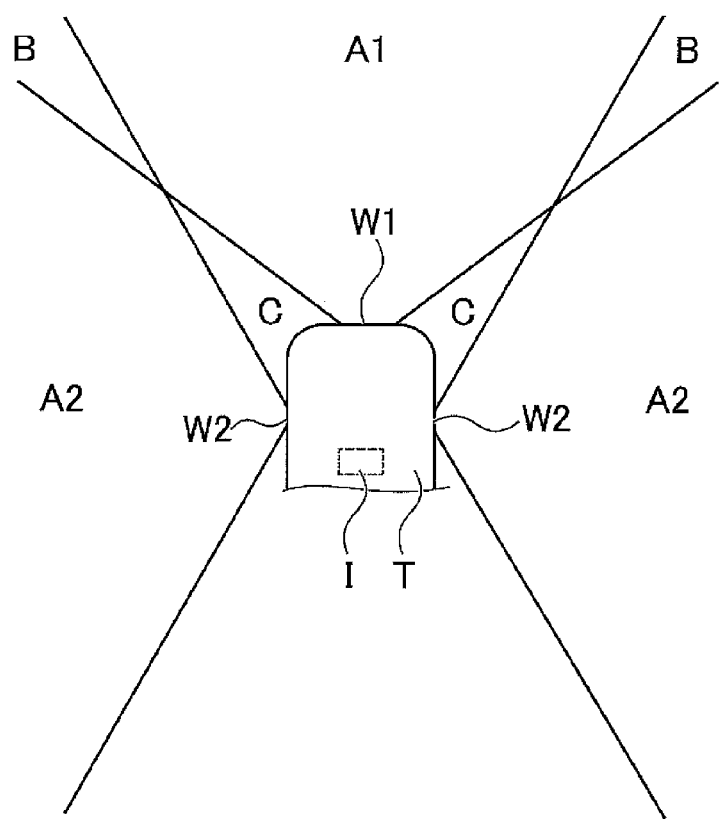
FIG. 1A is a view illustrating an example of a visual field range visible from a front window and a side window provided at a distal tip of an endoscope according to an embodiment.

The present invention relates to Japanese Patent Application No. 2020-79593 filed with the Japan Patent Office on Apr. 28, 2020, entire content of which is incorporated by reference in the specification.

Hereinafter, an endoscope system according to an embodiment will be described in detail.
(Overview of Endoscope System)

An endoscope system according to an embodiment includes an endoscope that captures a living tissue in a body cavity, and an image processing unit that performs image processing on a captured image captured by the endoscope. The endoscope includes an image sensor configured to capture an image of the living tissue, and an objective lens provided on a front side of a light receiving surface of the image sensor and configured to form the image of the living tissue on the light receiving surface. Here, the image processing unit includes a three-dimensional expansion processor. The three-dimensional expansion processor calculates information on different directions of a feature part (hereinafter, referred to as line-of-sight directions toward the feature part) visible from at least two different capturing positions or visible through at least two different windows based on position information of the feature part that is included in common in at least two captured images captured at the different capturing positions by the endoscope or that is included in common in one captured image obtained by integrating at least two images having different visual field ranges and captured through the different windows. The feature part is a part distinguishably identified with respect to other parts other than the feature part, and is, for example, a portion that can be distinguishably identified by a color component of the living tissue. For example, with respect to a healthy site showing a yellow color or a green color due to a mucous membrane on a surface of a living tissue, an inflamed site showing a red color due to edema or easy bleeding or an ulcerative site showing a white color due to white coating or mucopus can be used as a feature part.

Further, the image processing unit is configured to expand two-dimensional information of an image of the feature part to three-dimensional information using the calculated information on the line-of-sight directions toward the feature part.

The three-dimensional information is, for example, information including position information in a depth direction of a captured image of the feature part in addition to the two-dimensional position information of an inner surface in an organ. The position information in the depth direction can be obtained in addition to the two-dimensional information using a common feature part appearing in at least two captured images at different capturing positions or using a common feature part appearing in one captured image obtained by integrating images visible through at least two windows (appearing in an overlapping area of two visual field ranges).

When the three-dimensional information obtained in this way is used, the image of the feature part can be displayed on a monitor as a three-dimensional shape by performing rendering processing or the like. Further, it is possible to cause the monitor to display an image in which images of the two feature parts appearing in the captured images since the feature part is located in the overlapping area are converted into one image of the feature part.

FIG. 1A is a view illustrating an example of a visual field range visible from a front window W1 and a side window W2 provided at a distal tip T of the endoscope according to the embodiment. The side window W2 is provided so as to make a round along the outer periphery of the distal tip T that has a cylindrical shape. The front window W1 is a window which is provided on the front side of the light receiving surface of an image sensor I provided at the distal tip T and through which an area in the forward direction (upward direction in FIG. 1A) of the light receiving surface can be seen through the objective lens, and the side window W2 is a window which is provided in front of the light receiving surface of the image sensor I, and through which an area in a direction orthogonal to the front side (lateral direction illustrated in FIG. 1A) can be seen through the objective lens. The side window W2 in the present embodiment is a window facing the lateral side orthogonal to the front side, but may face any lateral side as compared with the front window W1. An orientation of the side window W2 (a direction in which a central axis of a visual field range viewed from the side window W2 is oriented) may be inclined from the front side by, for example, 30 degrees to 90 degrees.

An area A1 and areas B are present in the visual field range visible through the objective lens (not illustrated) provided in the front window W1 and the distal tip T, and areas A2 and the areas B are present in the visual field range visible through the objective lens (not illustrated) provided in the side window W2 and the distal tip T. Since the area B overlaps between the visual field range visible from the front window W1 and the visual field range visible from the side window W2, the area B is referred to as an overlapping area B hereinafter.

On the other hand, an illustrated area C is not included in the visual field ranges visible from the front window W1 and the side window W2. That is, an object in the area C is not included in any visual field range, the object does not appear in captured images of the image sensor I. Hereinafter, the area C is referred to as a blind spot area C.

Figure 1B:
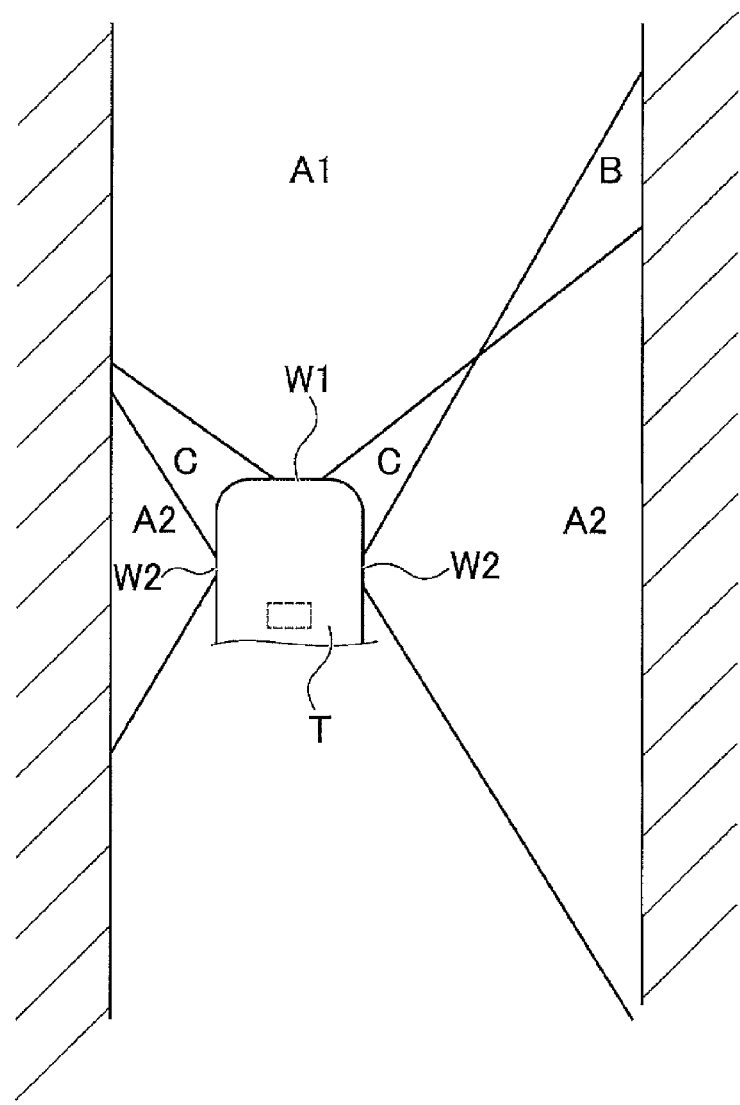
FIG. 1B is a view illustrating an example of a lateral position in an organ of the distal tip of the endoscope illustrated in FIG. 1A and a difference in the right-and-left direction of the visual field range at that time.

FIG. 1B is a view illustrating an example of a lateral position of the distal tip T of the endoscope in an organ and a difference in the right-and-left direction of the visual field range at that time. As illustrated in FIG. 1B, a visual field range of a surface of a living tissue in the organ varies depending on the lateral position of the distal tip T in the organ. The entire visual field range visible from the front window W1 and the side window W2 on the right side in FIG. 1B includes the area A1, the overlapping area B, and the area A2. The entire visual field range visible from the front window W1 and the side window W2 on the left side in FIG. 1B includes the area A1 and the area A2 and does not include the blind spot area C because the distal tip T is located to be biased in the left direction in the organ. Therefore, the blind spot area C exists in the visual field range of the image sensor I.

Since the overlapping area B exists in the visual field range on the right side in the example illustrated in FIG. 1B, in a case where there is a feature part having a color different from other parts, for example, a lesion site, in the overlapping area B, the lesion site is located in the visual field visible from the front window W1 and the visual field visible from the side window W2. Therefore, the image sensor I can capture an image of the feature part visible from the front window W1 and an image of the feature part visible from the side window W2 as one image through the objective lens.

Figure 2A:
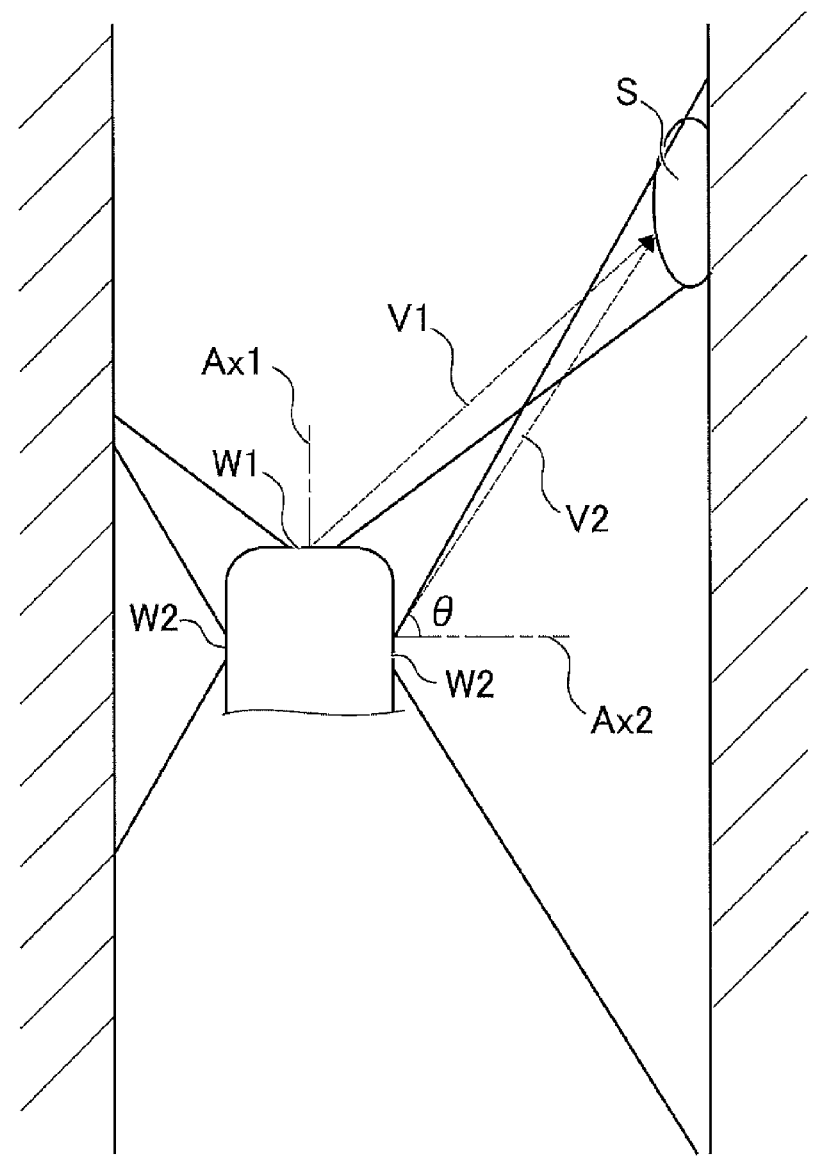
FIG. 2A is a view of a feature part of a living tissue, which illustrates a line-of-sight direction toward the feature part viewed from a front window and a side window.
Figure 2B:
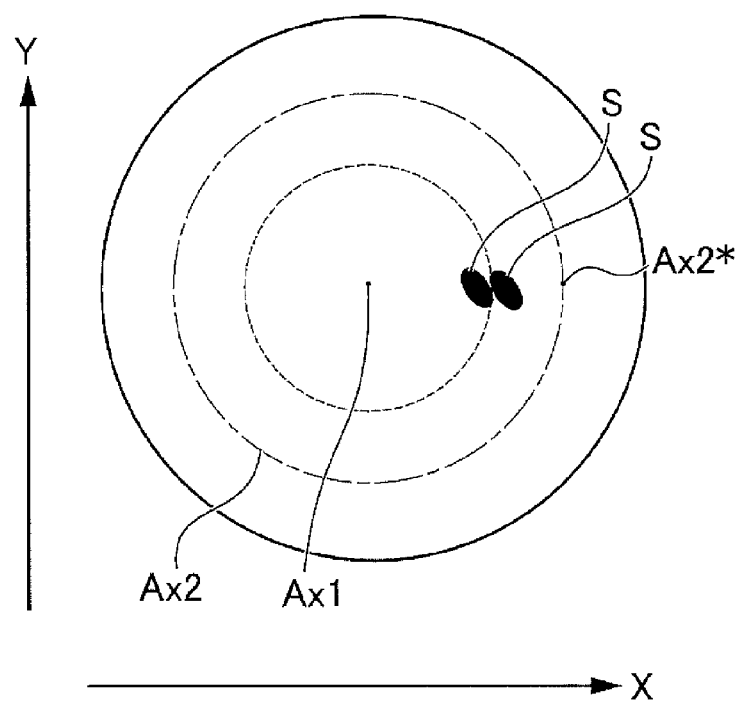
FIG. 2B is a view illustrating an example of a captured image of the feature part illustrated in FIG. 1A.

FIG. 2A is a view of a feature part S, which illustrates a line-of-sight direction toward the feature part S as viewed from the front window W1 and the side window W2. FIG. 2B is a view illustrating an example of a captured image of the feature part S illustrated in FIG. 2A.

FIGS. 2A and 2B illustrate a central axis Ax1 passing through a window center of the front window W1 and extending in the normal direction of a window surface, and a central axis Ax2 passing through a window center of a window width of the side window W2 and extending in the normal direction of a window surface. The central axis Ax1 is located on an extension line of an optical axis of the objective lens to be described later, and thus, appears as a point in the captured image. On the other hand, the side window W2 is provided so as to make a round on the circumference of the cylindrical distal tip T, and thus, appears as a circumferential shape in the captured image.

As illustrated in FIG. 2A, two images of the feature part S appear in the captured image as illustrated in FIG. 2B since the feature part S is located in the overlapping area B. When two images of the feature part S appear in the captured image, the three-dimensional expansion processor immediately obtains position information in the depth direction (forward) from the two images of the feature part S on the basis of the principle of triangulation using lines of sight V1 and V2 toward the feature part S.

Note that the depth direction viewed from the front window W1 and the side window W2 is not the upward direction but an inclination direction inclined from the upward direction to the lateral direction in the example illustrated in FIG. 2A, and a distance and a direction from the window center of the front window W1 to the feature part S, for example, can be obtained using the lines of sight V1 and V2 toward the feature part S. Therefore, position information in the height direction from the surface in the organ of the feature part S with a boundary part between the feature part S and a non-feature part as a reference can be obtained by using the distance and the direction of the feature part S. Further, position information in the forward direction (upward direction in FIG. 2A) from the window center of the front window W1 to the feature part S can be also obtained.

In this way, when the feature part S enters the overlapping area B and the two images of the feature part S appear, the three-dimensional expansion processor immediately obtains the above-described three-dimensional information, and immediately obtains three-dimensional position information including the position information of the feature part S in the height direction protruding from the surface of the living tissue and the position information of the feature part S in the forward direction.

In the example of FIG. 2A, the distal tip of the endoscope captures the surface of the living tissue in the organ, for example, while moving downward, and thus, the feature part S is located in the area A2 of the visual field range of the side window W2 before the state illustrated in FIG. 2A in which the feature part S is located in the overlapping area B, so that only one image of the feature part S appears in the captured image. Thereafter, the two images of the feature part S appear in the captured image as illustrated in FIG. 2B. The captured image has a circular shape in consideration of the visual field range having a circular shape in the example illustrated in FIG. 2B, but may be displayed as a rectangular display screen obtained by cutting out a part of the circular shape on the monitor. Thereafter, the feature part S is located in the area A1, and thus, one image of the feature part S appears in the captured image.

Therefore, when the feature part S is located in the overlapping area B and the two images of the feature part S appear in the captured image, it is possible to create an image of the surface in the organ as if the area A1, the overlapping area B, and the areas A2 are viewed through one window, for example, the front window W1 by eliminating the overlapping area B. In addition, the three-dimensional information can be obtained immediately if the two images of the feature part S appear. Thus, when an image of the feature part S is displayed on the monitor, the three-dimensional information can be reflected in the image, that is, a three-dimensional image can be displayed. For example, since the information of the feature part S in the height direction is obtained, it is also possible to perform the rendering process of reproducing the surface unevenness of the feature part S with respect to a surrounding part.

Note that the above-described processing for expansion to the three-dimensional information is performed using information on line-of-sight directions toward the feature part S visible from the front window W1 and the side window W2, but a plurality of windows provided at different positions may be used without being necessarily limited to the front window W1 and the side window W2 as long as the principle of triangulation can be applied. For example, the plurality of windows may be provided on a distal surface of the distal tip T. Further, as long as the principle of triangulation can be applied, processing of expanding to three-dimensional information may be performed using two or more captured images captured at different capturing positions when the distal tip T is moved, for example, in an organ, in which images of the feature part S commonly appear. In this case, it is preferable to acquire at least distance information between capturing positions among pieces of information on the capturing positions in order to perform the processing for expansion to three-dimensional information. As a result, the three-dimensional information can be obtained using line-of-sight directions for the same feature part S and the acquired distance information.

Note that captured images viewed from three or more windows or captured images at three or more capturing positions may be used in order to obtain the three-dimensional information more accurately. In this case, information is excessive, and thus, it is preferable to perform a calculation so as to minimize a calculation error when the three-dimensional information is obtained by the principle of triangulation.

(Specific Form of Endoscope System)

Figure 3:
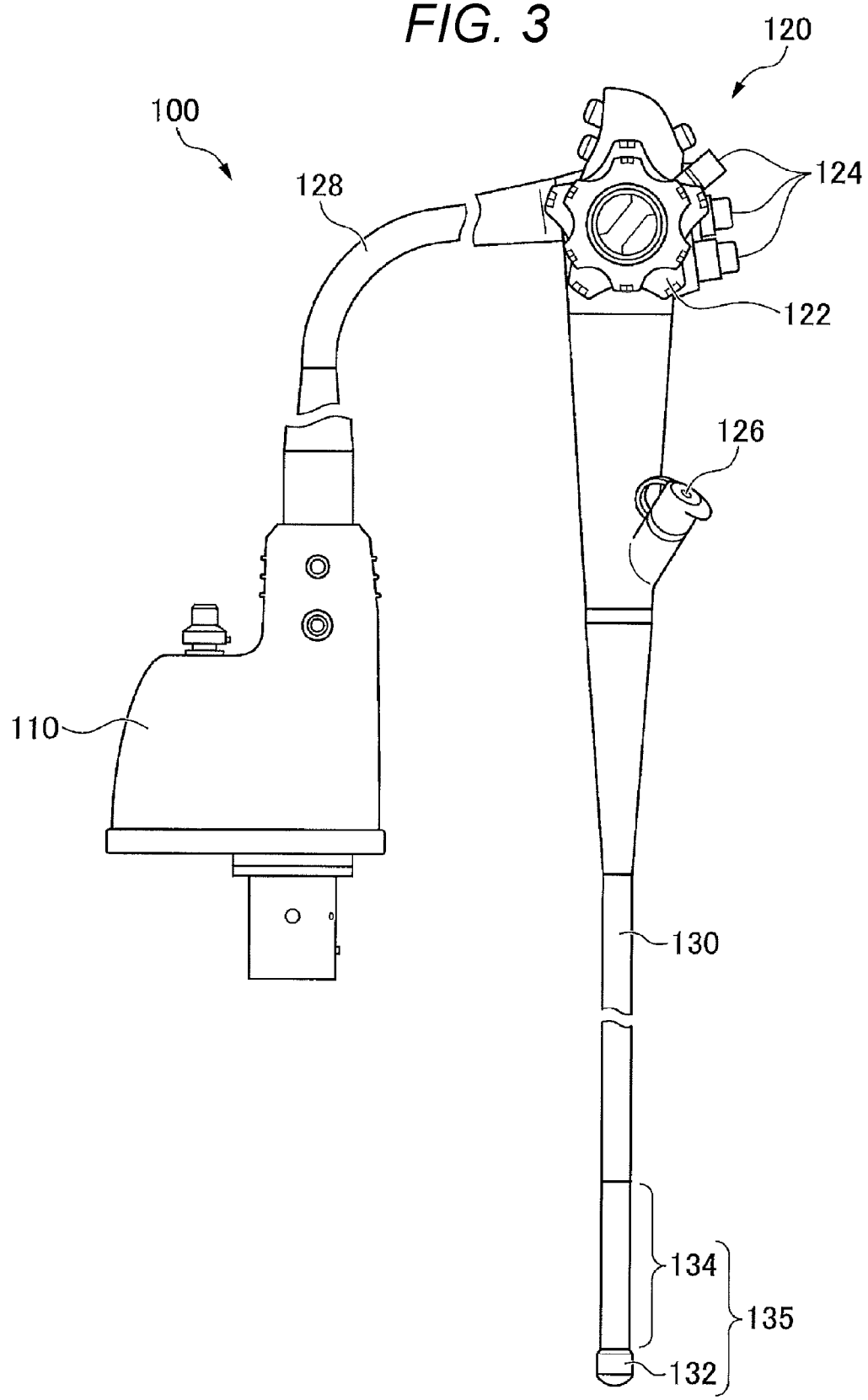
FIG. 3 is an external perspective view of an endoscope according to an embodiment.
Figure 4:
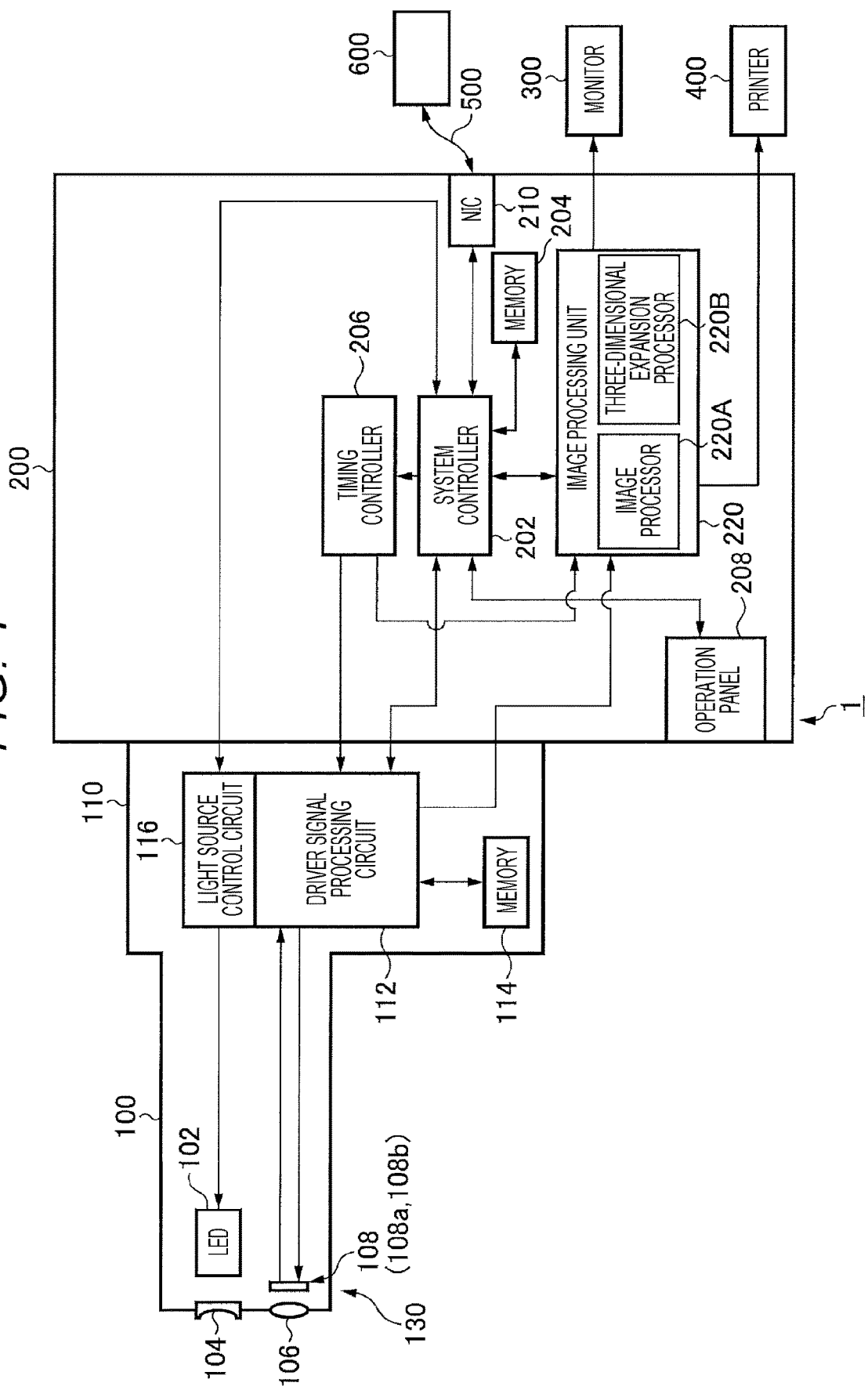
FIG. 4 is a block diagram illustrating a configuration of an endoscope system according to an embodiment.

FIG. 3 is an external perspective view of an endoscope according to an embodiment. FIG. 4 is a block diagram illustrating a configuration of an endoscope system according to an embodiment. FIG. 4 is a view illustrating an example of a configuration of the distal tip of the endoscope according to the embodiment.

An endoscope (hereinafter, referred to as an electronic scope) 100 illustrated in FIG. 3 is connected to a processor 200 for an electronic endoscope illustrated in FIG. 4 to form an endoscope system 1. The endoscope system 1 is a system specialized for medical use, and mainly includes the electronic scope 100, the processor 200 for an electronic endoscope, and a monitor 300 as illustrated in FIG. 4. Each of the electronic scope 100 and the monitor 300 is connected to the processor 200.

As illustrated in FIG. 3, the electronic scope 100 mainly includes a connector 110, an operation unit 120, and a distal tip 132, and further includes a flexible cable 130 that extends from the operation unit 120 toward the distal tip 132 on the front side and has flexibility, a bending tube 134 that is connected to the front side of the flexible cable 130 with a connecting portion interposed therebetween and freely bendable, and a universal tube 128 that extends rearward from the operation unit 120. The connector 110 is fixed to a rear end of the universal tube 128 and is configured to be connected to the processor 200.

A plurality of bending operation wires are inserted into the operation unit 120, the flexible cable 130, and the bending tube 134, a distal tip of each bending operation wire is connected to a rear end of the bending tube 134, and a rear end of each bending operation wire is connected to a bending operation knob 122 of the operation unit 120. The bending tube 134 is bent in any direction and at any angle according to the operation of the bending operation knob 122.

Further, the operation unit 120 includes a plurality of operation buttons 124. When an endoscope operator (surgeon or assistant) presses the operation button 124, the operation button 124 can instruct functions such as discharge of water and gas from an air/water supply port (not illustrated) provided on a distal surface of the distal tip 132, suction of liquid and gas in a living tissue through a suction port, and discharge of a cleaning liquid from a cleaning liquid discharge nozzle configured for cleaning of the objective lens. It is possible to determine an operation that is desired to be performed by pressing the operation button 124 in advance, and to assign a function for implementing the operation to the operation button 124.

The distal tip 132, at a distal end of the bending tube 134 is made of a hard resin material (for example, ABS, modified PPO, PSU, and the like) that is not substantially elastically deformed.

Inside the distal tip 132, an LED light source 102 and an image sensor 108 located immediately behind an objective lens 106 are provided. That is, the distal tip 132 provided at a distal end of the bending tube 134 includes the LED light source 102, the objective lens 106, and the image sensor 108. The objective lens 106 is provided on a front surface of the image sensor 108, and forms an image of a living tissue on a light receiving surface of the image sensor 108 in a visual field range of a viewing angle of 180 degrees or more, preferably more than 180 degrees. The distal tip 132 is provided with a front window facing the front side of the light receiving surface of the image sensor 108 and a side window facing the lateral side orthogonal to the front side as will be described later, and the image sensor 108 is configured to capture images formed on the light receiving surface by the objective lens 106 through the front window and the side window.

The flexible cable 130, the bending tube 134, and the distal tip 132 form an insertion portion 135 that is inserted into a body cavity. A cable for an image signal extending from the image sensor 108 provided at the distal tip 132 extends from the distal tip 132 to the inside of the connector 110 through the inside of the bending tube 134, the flexible cable 130, the operation unit 120, and the universal tube 128. The connector 110 is connected to the processor 200. The processor 200 processes an image signal transmitted from the image sensor and controls an image of an object captured by the image sensor 108 to be displayed on the monitor 300.

As illustrated in FIG. 4, the processor 200 of the endoscope system 1 includes a system controller 202 and a timing controller 206. The system controller 202 executes various programs stored in a memory 204 and integrally controls the entire electronic endoscope system 1. In addition, the system controller 202 changes various settings of the endoscope system 1 in accordance with an instruction of the endoscope operator (surgeon or assistant) which is input to an operation panel 208. The timing controller 206 outputs a clock pulse for adjusting an operation timing of each unit to each circuit in the endoscope system 1.

The distal tip 132 of the electronic scope 100 is provided with the LED light source 102 in addition to the image sensor 108. The LED light source 102 emits illumination light to illuminate a living tissue for capturing by the image sensor 108.

The LED light source 102 is driven by a drive signal generated by a light source control circuit 116 provided in the connector 110 to emit light. Instead of the LED light source 102, a laser element may be used, and a high-brightness lamp, for example, a xenon lamp, a metal halide lamp, a mercury lamp, or a halogen lamp may be used.

In the example illustrated in FIG. 4, the LED light source 102 is provided in the distal tip 132, but may be provided as a light source device in the connector 110 or the processor 200. In this case, from the light source device to the distal tip 132, the illumination light is guided to the distal tip 132 through a light guide in which a plurality of fiber cables are bundled.

The light emitted from the LED light source 102 is emitted as the illumination light to a living tissue, which is the object, via a light distribution lens 104. Light reflected from the living tissue forms optical images on the light receiving surface of the image sensor 108 through the front window 140, the side window 150 (see FIG. 5), and the objective lens 106.

The image sensor 108 is, for example, a single-plate color CCD (Charge-Coupled Device) image sensor in which various filters such as an IR (Infrared) cut filter 108a and a Bayer-arranged color filter 108b are arranged on the light receiving surface, and generates primary color signals of R (Red), G (Green), and B (Blue) according to the optical image formed on the light receiving surface. Instead of the single-plate color CCD image sensor, a single-plate color complementary metal oxide semiconductor (CMOS) image sensor can be used. In this way, the electronic scope 100 uses the image sensor 108 to image a living tissue inside an organ and generate a moving image.

The electronic scope 100 includes a driver signal processing circuit 112 provided inside the connector 110. The driver signal processing circuit 112 generates an image signal (brightness signal Y or color difference signal Cb or Cr) by performing predetermined signal processing such as color interpolation or a matrix calculation on the primary color signal input from the image sensor 108, and outputs the generated image signal to an image processing unit 220 of the processor 200 for an electronic endoscope. In addition, the driver signal processing circuit 112 accesses the memory 114, and reads specific information of the electronic scope 100. For example, the specific information of the electronic scope 100 recorded in the memory 114 includes the number of pixels or sensitivity of the image sensor 108, a frame rate with which the electronic scope 100 is operable, and a model number. The driver signal processing circuit 112 outputs the specific information read from the memory 114 to the system controller 202.

The system controller 202 performs various calculations based on the information stored in the memory 204 and the device-specific information of the electronic scope 100, and generates a control signal. The system controller 202 controls an operation and a timing of each circuit inside the processor 200 for an electronic endoscope by using the generated control signal so that processing suitable for the electronic scope 100 connected to the processor 200 for an electronic endoscope is performed.

The timing controller 206 supplies the clock pulse to the driver signal processing circuit 112, the image processing unit 220, and the light source unit 230 in accordance with timing control of the system controller 202. The driver signal processing circuit 112 performs driving control of the image sensor 108 at a timing synchronized with the frame rate of the video image processed on the processor 200 for an electronic endoscope side in accordance with the clock pulses supplied from the timing controller 206.

The image processing unit 220 includes an image processor 220A (see FIG. 4) that generates a video signal for displaying an image or the like on the monitor based on the image signal input from the driver signal processing circuit 112 and outputs the video signal to the monitor 300 under the control of the system controller 202.

The image processing unit 220 further includes a three-dimensional expansion processor 220B (see FIG. 4) configured to expand two-dimensional information of an image of a feature part in a captured image obtained by the image sensor 108 to three-dimensional information. The three-dimensional expansion processor 220B will be described later. In addition, the image processor 220A may perform, on an image of a living tissue obtained by the electronic scope 100, numerical processing for quantifying a feature amount of each pixel of the image in which a lesion site can be distinguished from a healthy site to evaluate the degree of progression of the lesion site of the image, and further generate a color map image in which a numerical value of each pixel obtained by the numerical processing is replaced with a color. In this case, the image processor 220A generates a video signal for displaying information on a result of the numerical processing and the color map image on the monitor, and outputs the video signal to the monitor 300. As a result, the endoscope operator can accurately perform an examination through the image displayed on a display screen of the monitor 300. The image processor 220A outputs the image, the information on the result of the numerical processing, and the color map image to the printer 400 as necessary.

The processor 200 is connected to a server 600 via a network interface card (NIC) 210 and a network 500. The processor 200 can download information regarding an examination using the endoscope (for example, electronic medical chart information of a patient or information of the surgeon) from the server 600. For example, the downloaded information is displayed on the display screen of the monitor 300 or the operation panel 208. In addition, the processor 200 can cause the server 600 to store an examination result by uploading the examination result of the electronic scope 100 to the server 600.

Figure 5:
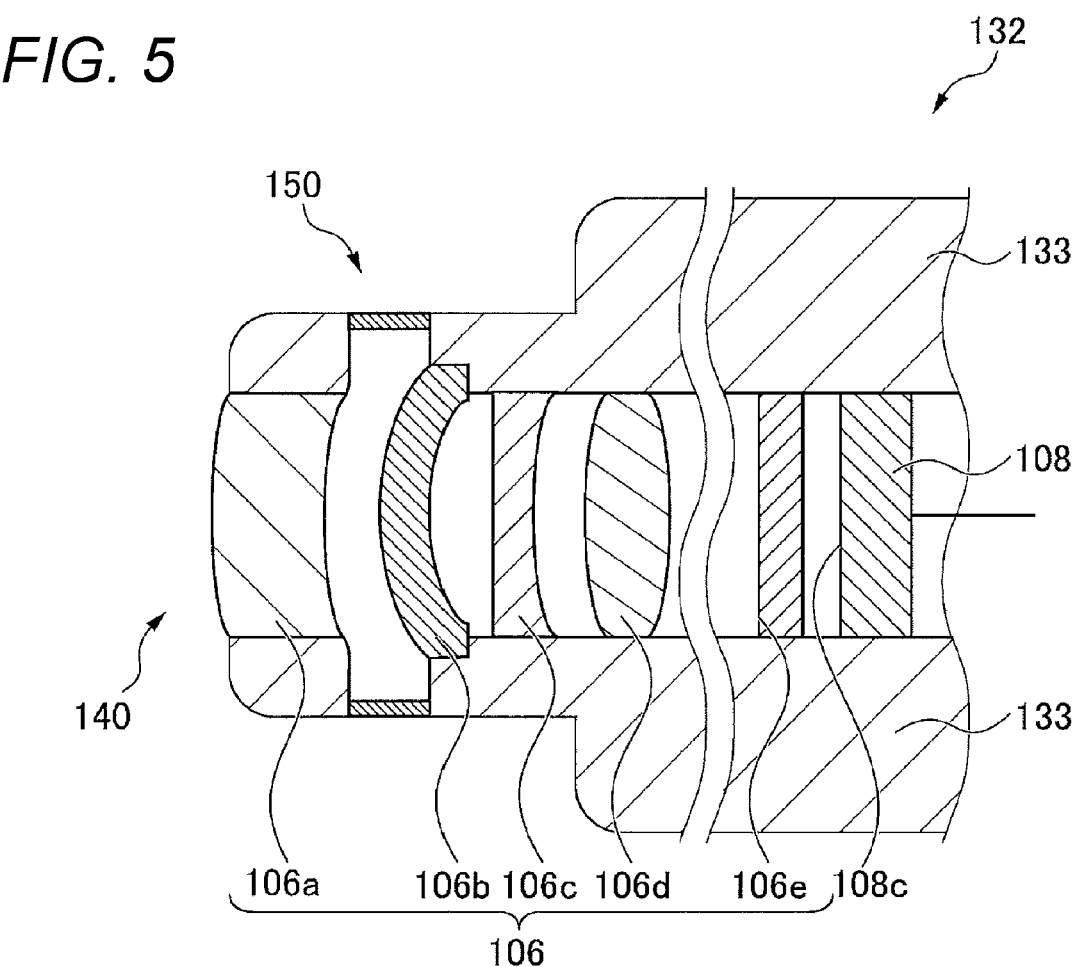
FIG. 5 is a view illustrating an example of a configuration of a distal tip of an endoscope according to an embodiment.

FIG. 5 is a view illustrating an example of an internal structure of the distal tip 132.

The distal tip 132 includes the objective lens 106, the image sensor 108, the front window 140, and the side window 150. The objective lens 106 and the image sensor 108 are disposed in a cylindrical member 133, which is made of a hard resin material, of the distal tip 132. The distal tip 132 corresponds to the distal tip T in the example illustrated in FIGS. 1A, 1B, and 2A.

The front window 140 faces the front direction of a light receiving surface 108c of the image sensor 108. The side window 150 faces the lateral side orthogonal to the front side. The side window 150 faces the lateral side orthogonal to the front side, but it is sufficient if the side window 150 faces any lateral side as compared with the front window 140.

The objective lens 106 includes a lens group of lenses 106a to 106e including a meniscus lens, a convex lens, and a concave lens, and a half angle of view thereof is more than 90 degrees, preferably 110 degrees or more. Therefore, the objective lens 106 simultaneously forms a front-view image of a living tissue obtained through the front window 140 and a side-view image of the living tissue obtained through the side window 150 on the light receiving surface 108c as captured images. The surface of the lens 106a on an object side also serves as the front window 140. The side window 150 is provided with a cover glass.

As illustrated in FIG. 1A, visual field ranges visible from the front window 140 and the side window 150 of the distal tip 132 includes the area A1, the overlapping areas B, and the areas A2. Further, there is the blind spot area C where the object is not visible from the front window 140 and the side window 150. Since the front-view image obtained through the front window 140 and the side-view image obtained through the side window 150 are simultaneously captured as the image of the living tissue, there is a case where the feature part S appears as two images in a captured image as illustrated in FIG. 2B.

The image processing unit 220 includes the three-dimensional expansion processor 220B that obtains three-dimensional information of the feature part S from two-dimensional information (an x-coordinate position and a y-coordinate position on the captured image) of the two images of the feature part S appearing in the captured image.

The three-dimensional expansion processor 220B calculates line-of-sight directions toward the feature part S visible through the front window 140 and the side window 150 in the captured image captured by the electronic scope 100 based on position information in each of the two images of the feature part S included in common in the two images (front-view image and side-view image) obtained through the front window 140 and the side window 150, an expands the two-dimensional information of the images of the feature part S to the three-dimensional information using the calculated line-of-sight directions. Whether or not the two images obtained through the front window 140 and the side window 150 are common can be determined by positions of the two feature parts S in the captured image and color information of the feature part S or outline shape information of the feature part S. In addition, in a case where a surface in a living tissue is captured while moving the distal tip 132 of the electronic scope 100 in one direction, the feature part S moves from the area A2 to the overlapping area B, and thus, whether or not two common feature parts S appear in the captured image can be easily determined using a plurality of the captured images generated in time series.

Note that the two-dimensional information of the images of the feature part S can be expanded to three-dimensional information not only in a case where capturing is performed while moving the distal tip 132 of the electronic scope 100 in one direction, but also in a case where the bending tube 134 is captured while being bent.

The three-dimensional expansion processor 220B obtains an azimuth direction of each position of interest of the feature part S with respect to the central axis Ax1 of the front window 140 from coordinate positions in an X direction and a Y direction (in an XY coordinate system illustrated in FIG. 2B and having the X direction and the Y direction as coordinate axes) which correspond to two-dimensional information of each position of interest of the feature part S in the front-view image obtained through the front window 140. Since the central axis Ax1 is set to coincide with the optical axis of the objective lens 106, the azimuth direction of the feature part S in the captured image coincides with an azimuth direction of the distal tip 132 in the organ viewed from the front window 140. In the example illustrated in FIG. 2B, the right lateral direction with respect to the central axis Ax1 is the azimuth direction of the position of interest of the feature part S. Similarly, the three-dimensional expansion processor 220B obtains an azimuth direction from a center point Ax2* of the central axis Ax2 of the side window 150 of each position of interest of the feature part S in the captured image viewed from the side window 150. The central axes Ax1 and Ax2 are axes extending from the window centers of the front window 140 and the side window 150 in the normal direction of the window surfaces.

Regarding the position of interest when the azimuth direction with respect to the central axis Ax1 is obtained and the position of interest when the azimuth direction from the center point Ax2* is obtained, the same position is specified by using color information of a pixel value or the outline shape information of the feature part S. In addition, since the side-view image and the front-view image are images obtained using the same objective lens 106, the azimuth direction of the position of the feature part S in the side-view image viewed from the central axis Ax1 coincides with the azimuth direction of the same position of the same feature part S in the front-view image viewed from the central axis Ax1. Thus, the center point Ax2* is an intersection point where a straight line connecting the position of interest of the feature part S and the central axis Ax1 (point illustrated in FIG. 2B) on the extension line of the optical axis of the objective lens 106 intersects the central axis Ax2 (circle with a one-dot chain line illustrated in FIG. 2B).

On the other hand, the central axis Ax2 is an axis extending in the normal direction from the window center of the side window 150, and thus, position coordinates of a position of interest with the center point Ax2* in the side-view image as the reference are obtained, and an angle θ indicating an elevation angle direction (upward direction (forward direction) with respect to the lateral direction of FIG. 2A) illustrated in FIG. 2A is calculated from the position coordinate based on lens characteristics of the objective lens 106. As a result, it is possible to obtain the directions of the lines of sight V1 and V2 toward the feature part S illustrated in FIGS. 2A and 2B.

Further, positions of the window center of the front window 140 and the window center of the side window 150 at the distal tip 132 are known, and thus, the three-dimensional expansion processor 220B calculates a position where the line of sight V1 toward the feature part S intersects the line of sight V2 toward the feature part S based on the principle of triangulation from these positions and the obtained directions of the lines of sight V1 and V2 toward the feature part S.

Therefore, the three-dimensional expansion processor 220B can calculate the azimuth direction and the elevation angle direction of each position of interest of the feature part S from the window center of the front window 140 or the window center of the side window 150, and the distance information. The three-dimensional expansion processor 220B can calculate the position information of the feature part S with respect to the distal tip 132 along an extending direction of the organ, for example, from the azimuth direction, the elevation angle direction, and the distance information, and further calculate distance information along the lateral direction (the lateral direction illustrated in FIG. 2A) from the window center of the front window 140 or the side window 150 to the position of interest of the feature part S. As a result, the three-dimensional information of the feature part S is obtained.

When the captured image illustrated in FIG. 2B is obtained, the image processing unit 220 obtains the three-dimensional information of the feature part S as described above, but can also eliminate the overlapping area B from the captured image, and perform a process of creating an image of the surface in the organ as if the area A1, the overlapping area B, and the area A2 are viewed through the front window W1 to display the created image on the monitor 300. In this case, the image of the feature part S can be displayed on the monitor 300 as a stereoscopic image by performing three-dimensional processing using the acquired three-dimensional information of the feature part S. Since information in the height direction of the feature part S can be obtained using the distance information along the lateral direction from the window center of the front window 140 to the position of interest of the feature part S, for example, rendering processing for reproducing the surface unevenness of the feature part S can be performed as the three-dimensional processing. Since the feature part S can be displayed on the monitor 300 as the stereoscopic image in this way, it is useful for determining and diagnosing whether or not the feature part S is a malignant tumor that requires resection.

In addition, in a case where it is known by a previous diagnosis that there is a lesion site at a base part of folds in an organ such as a large intestine having the folds on an inner surface, the above-described endoscope system can be also used to obtain the information of the surface unevenness of the lesion site by disposing the distal tip 132 such that the lesion site is located in the overlapping area B and obtaining the three-dimensional information of the lesion site using the above-described method.

Although the two-dimensional information of the image of the feature part S is expanded to the three-dimensional information using the images of the living tissue viewed from the front window 140 and the side window 150 in the above-described embodiment, the windows provided at the distal tip 132 are not limited to the front window 140 and the side window 150, and a plurality of front windows provided at different positions in the distal tip 132 may be used, or a plurality of side windows provided at different positions in the distal tip 132 may be used. In this case, two windows are provided at different positions of the distal tip 132, and thus, capturing positions are different from each other. Therefore, based on position information of the feature part S included in common in captured images captured at the at least two capturing positions, the three-dimensional expansion processor 220B can expand the two-dimensional information of the image of the feature part S to the three-dimensional information using line-of-sight directions toward the feature part S visible at the different capturing positions.

The capturing positions may be different positions obtained by moving the electronic scope 100 with respect to the living tissue, for example, different positions in the extending direction of the organ. In this case, the three-dimensional expansion processor 220B preferably calculates the three-dimensional information using different directions in which the feature part S is visible caused by different capturing positions and distance information between the capturing positions. The distance information between the capturing positions may be obtained from information of the capturing positions of the distal tip 132 from a position measurement system of the electronic scope 100. For example, the position measurement system is a system that acquires a position of the image sensor 108 located at the distal tip 132 of the electronic scope 100 inserted into the organ, and further, each subsequent position of the flexible cable 130 using a magnetic sensor or a system that acquires an insertion length of the electronic scope 100 inserted from an open end of the organ.

As in the above-described embodiment, preferably, the objective lens 106 is configured to simultaneously form the front-view image of the living tissue obtained through the front window 140 and the side-view image of the living tissue obtained through the side window 150 on the light receiving surface as the captured image, and the three-dimensional expansion processor 220B is configured to calculate the line-of-sight directions toward the feature part S visible through the front window 140 and the side window 150 based on the position information of the feature part S in the front-view image and the position information of the feature part S in the side-view image, the feature part S being included in common in the front-view image and the side-view image in the captured image, and to expand the two-dimensional information to the three-dimensional information using the calculated line-of-sight directions. Since the front window 140 and the side window 150 have directions orthogonal to each other as directions of the central axes of the visual field ranges, the three-dimensional information can be calculated more accurately.

As described above, the images captured through the different windows (front window 140 and side window 150) include the overlapping area B including the same part of the living tissue, and the position information in each image of the feature part S is information obtained when the feature part S is located in the overlapping area B. Therefore, the three-dimensional information can be accurately calculated from the position information of each position of the image of the feature part S in one captured image.

As described above, the line-of-sight directions toward the feature part S are different if there are two or more positions as the capturing positions. Thus, when the image sensor 108 continuously captures the living tissue, a plurality of images including the same feature part S may be captured images having mutually different capturing positions before and after the distal tip 132 of the electronic scope 100 is moved in the body cavity. Here, the mutually different capturing positions mean that the capturing positions are different from each other in the extending direction of the organ.

Figure 6:
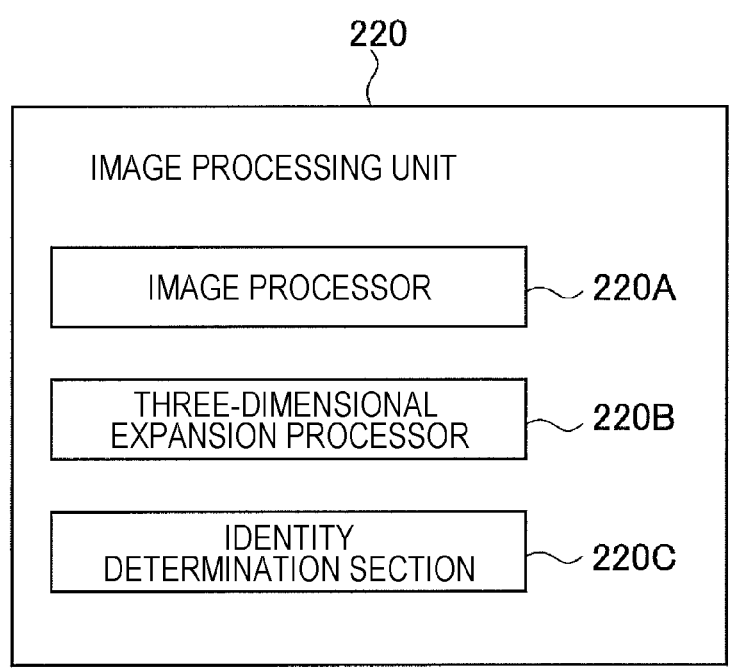
FIG. 6 is a view illustrating an example of a configuration of an image processing unit of an endoscope system used in an embodiment.

According to an embodiment, the image processing unit 220 preferably includes an identity determination section 220C in addition to the image processor 220A and the three-dimensional expansion processor 220B as illustrated in FIG. 6. FIG. 6 is a view illustrating an example of a configuration of the image processing unit of the endoscope system used in the embodiment. The identity determination section 220C is configured to determine whether or not the feature part S included in each of the plurality of images (for example, the front-view image and the side-view image) is identical using at least one of the color information of the feature part S and the outline shape information of the feature part S. In a case where a moving image is captured, an image of the feature part S moves in one direction in the captured image, and thus, it is possible to easily determine whether or not the feature part S is identical. However, in a case where a plurality of feature parts S exist, there is also a case where it is difficult to specify whether or not the feature part S is identical. Therefore, it is preferable that the identity determination section 220C determine whether or not the feature part S is identical when the three-dimensional information of the feature part S is calculated.

According to an embodiment, preferably, the three-dimensional expansion processor 220B includes a predictive model obtained by machine learning of a relationship between the two-dimensional information and the three-dimensional information using, as training data, the two-dimensional information and the three-dimensional information of images of the feature part S in a plurality of captured images including the feature part S of the living tissue that have been captured so far in the electronic scope 100. Preferably, the predictive model is configured to acquire the three-dimensional information by inputting the two-dimensional information of the image of the feature part S in the captured image currently captured by the electronic scope 100 to the predictive model. The three-dimensional information including the information of the surface unevenness of the feature part S can be predicted based on the color information and the size of the feature part S which are included in the two-dimensional information. For machine learning of the predictive model, for example, deep learning by a neural network is used. In addition, a random forest using a tree structure can be also used as a part of the predictive model. As the predictive model, a known model such as a convolutional neural network or a stacked auto-encoder can be used.

Figure 7:
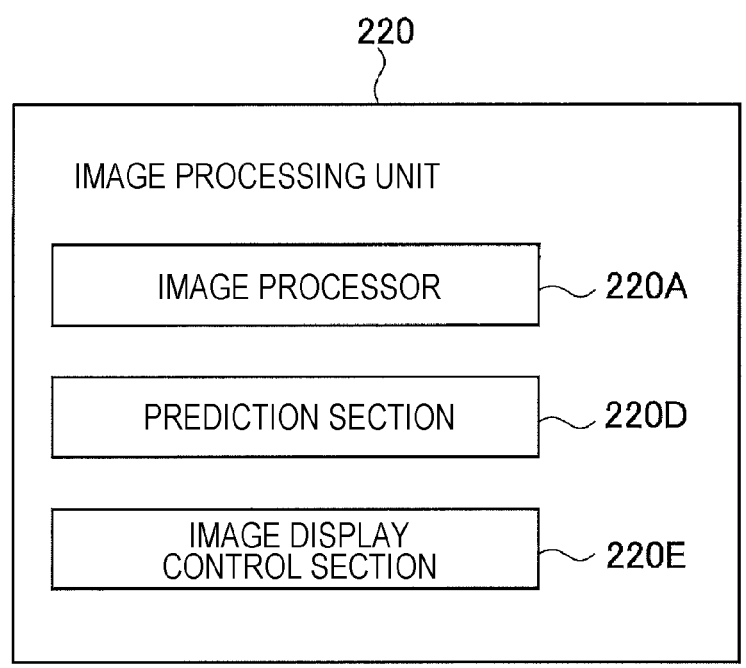
FIG. 7 is a view illustrating an example of a configuration of an image processing unit of an endoscope system used in an embodiment.

With such a predictive model obtained by the machine learning is provided, it is possible to obtain the three-dimensional information of the feature part S without calculating the directions of the line of sight V1 and V2 toward the feature part S by the three-dimensional expansion processor 220B. Therefore, according to an embodiment, the image processing unit 220 does not include the three-dimensional expansion processor 220B, but includes a prediction section 220D, as illustrated in FIG. 7. FIG. 7 is a view illustrating an example of a configuration of the image processing unit of an endoscope system used in the embodiment. The prediction section 220D preferably includes a predictive model configured to predict three-dimensional information from two-dimensional information by inputting the two-dimensional information of the image of the feature part S included in a captured image captured by the electronic scope 100. The predictive model is a model that is obtained by machine learning of a relationship between the two-dimensional information of an image of the feature part S and the three-dimensional information of the feature part S in the captured image using the known two-dimensional information of the image of the feature part S in a plurality of known captured images including the feature part S and the corresponding known three-dimensional information of the feature part S as training data. For machine learning of the predictive model, for example, deep learning by a neural network is used. In addition, a random forest using a tree structure can also be used as a part of the predictive model. As the predictive model, a known model such as a convolutional neural network or a stacked auto-encoder can be used.

According to the embodiment, the image processing unit 220 includes an image display control section 220E. When the image sensor 108 continuously captures a living tissue as a moving image and displays an image on the monitor 300 using three-dimensional information obtained by the prediction section 220D from the captured image, an object in the blind spot area C is not displayed. Preferably, the image display control section 220E performs control to display a three-dimensional image of the entire feature part S on the monitor 300 by using the three-dimensional information predicted from the two-dimensional information of the image of the feature part S included in the captured image before at least a part of the feature part S is located in the blind spot area C when the at least part of the feature part S is located in the blind spot area C. The three-dimensional image is, for example, an image subjected to rendering processing.

Further, preferably, the image display control section 220E performs control to display one image of the entire feature part S and the three-dimensional image using the three-dimensional information predicted from the two-dimensional information of the image of the feature part S included in the captured image before at least a part of the feature part S is located in the overlapping area B when the at least part of the feature part S is located in the overlapping area B.

Figure 8A:
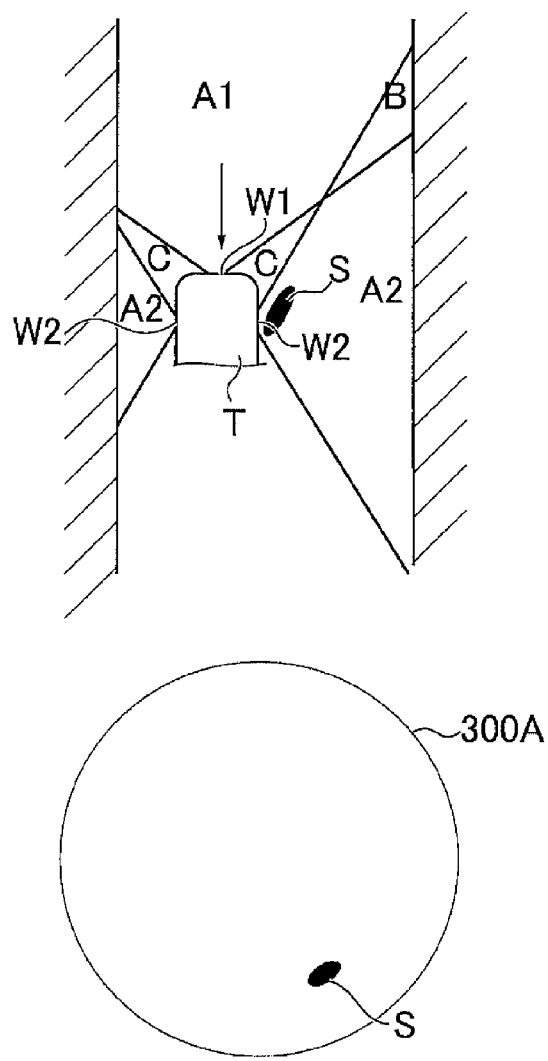
FIG. 8A is a view illustrating a position of the distal tip of the endoscope with respect to the feature part and an example of the captured image displayed on the monitor in time series.
Figure 8B:
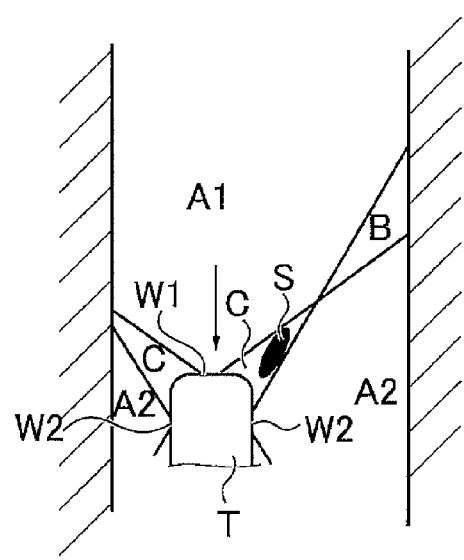
FIG. 8B is a view illustrating a position of the distal tip of the endoscope with respect to the feature part and an example of the captured image displayed on the monitor in time series.
Figure 8B:
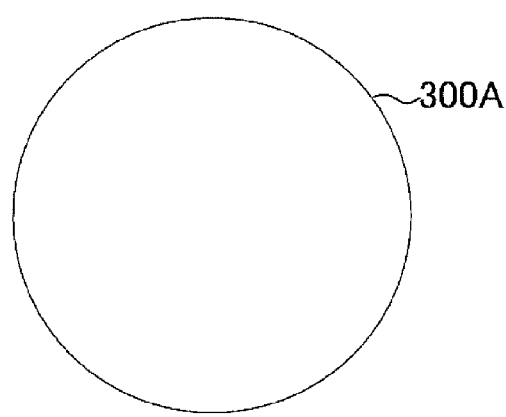
Figure 8C:
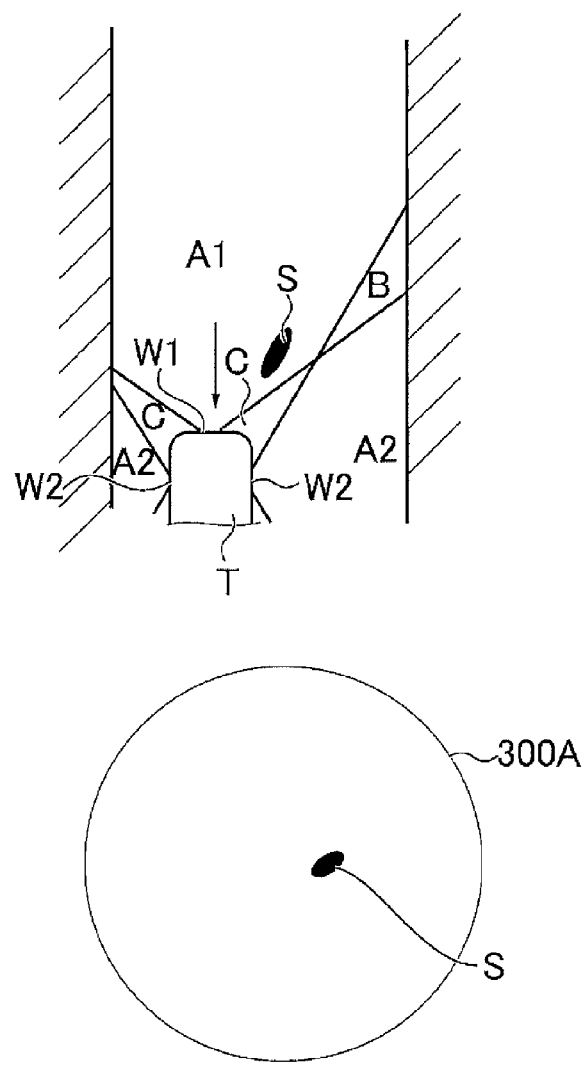
FIG. 8C is a view illustrating a position of the distal tip of the endoscope with respect to the feature part and an example of the captured image displayed on the monitor in time series.

FIGS. 8A to 8C are views illustrating positions of the distal tip T with respect to the feature part S and examples of captured images in time series. The upper part in FIGS. 8A to 8C illustrates the position of the distal tip T with respect to the feature part S, and the lower part in FIGS. 8A to 8C illustrates an example of a display screen 300A of the monitor. Note that the examples illustrated in FIGS. 8A to 8C are described using the example illustrated in FIG. 1B.

When a surface of a living tissue is continuously captured while the electronic scope 100 inserted into the deepest portion of an examination target part in an organ is pulled downward as illustrated in FIGS. 8A to 8C, the feature part S is initially located in the area A2 of the visual field range of the side window W2 as illustrated in FIG. 8A, and thus, the feature part S appears on the display screen 300A of the monitor. Thereafter, when the electronic scope 100 is moved, the feature part S enters the blind spot area C as illustrated in FIG. 8B. Therefore, the feature part S disappears from the display screen 300A. When the electronic scope 100 is further moved, the feature part S enters the area A1 as illustrated in FIG. 8C. Therefore, the feature part S appears again on the display screen 300A.

As illustrated in FIG. 8B, when the feature part S is located in the blind spot area C, the image display control section 220E performs control to display the image of the entire feature part S on the monitor 300 as the three-dimensional image by using the three-dimensional information predicted by the prediction section 220D from the two-dimensional information of the image of the feature part S located in the area A2 before being located in the blind spot area C. Therefore, the image display control section 220E extracts an edge area of the feature part S based on the color information, and monitors that the extracted edge area moves with the lapse of time. When at least a part of the feature part S enters the blind spot area C, the image display control section 220E performs control to display the image of the entire feature part S on the monitor 300 as the three-dimensional image using the three-dimensional information predicted by the prediction section 220D.

Further, the image display control section 220E can also monitor the movement of the feature part S from which the edge area is extracted based on the color information, and perform control to create an image such that there is one image of the feature part S and display the image of the feature part S as the three-dimensional image created using the three-dimensional information predicted by the prediction section 220D when at least a part of the feature part S enters the overlapping area B.

Figure 9A:
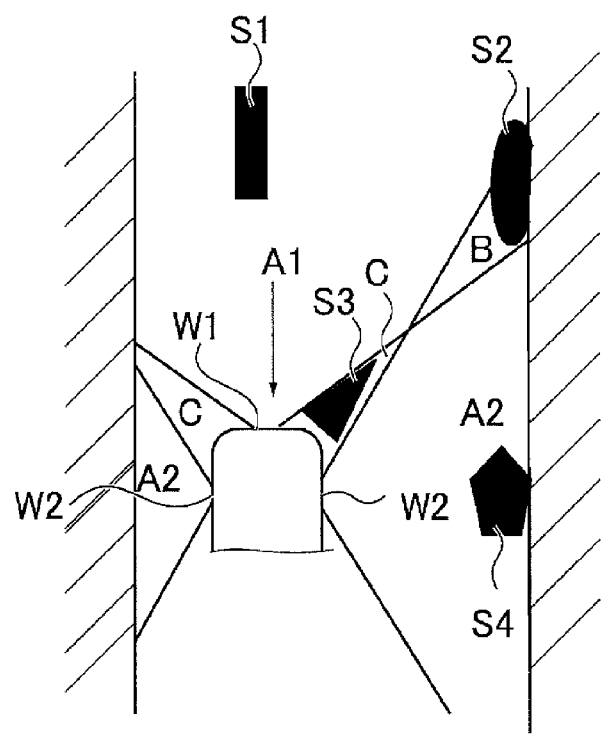
FIG. 9A is a view illustrating an example of the position of the distal tip of the endoscope with respect to the feature part.
Figure 9B:
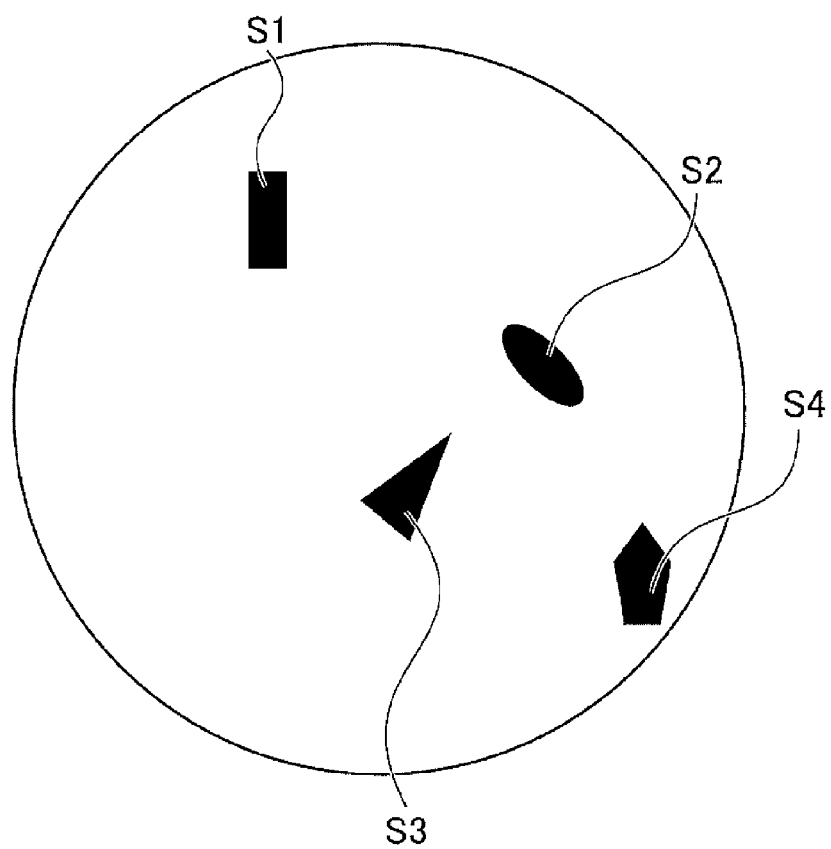
FIG. 9B is a view illustrating an example of an image displayed on the monitor of the endoscope system according to the embodiment.

FIG. 9A is a view illustrating an example of a position of the distal tip T with respect to the feature part S, and FIG. 9B is a view illustrating an example of an image displayed on the monitor of the endoscope system according to the embodiment. As illustrated in FIG. 9A, there are feature parts S1 to S4 on a surface of a living tissue, the feature part S1 is located in the area A1, the feature part S2 is located in the overlapping area B, the feature part S3 is located in the blind spot area C, and the feature part S4 is located in the area A2.

In this case, regarding the feature part S2 located in the overlapping area B, two images do not appear on the image display and one image is displayed, and the feature part S3 located in the blind spot area C appears on the image display without disappearing. All the images of the feature parts S1 to S4 are three-dimensional images.

It is preferable that a form of the image display as illustrated in FIG. 9B in which the feature parts S1 to S4 are displayed as the three-dimensional images be selected by pressing the operation button 124 of the operation unit 120 (see FIG. 3). Therefore, the image display on the monitor 300 is preferably switched at any time by the operation button 124 between the display as illustrated in FIG. 9B and a display of a conventional captured image using two-dimensional information in which the two images of the feature part S2 in the overlapping area B appear and the feature part S3 in the blind spot area C is not displayed.

Note that the three-dimensional expansion processor 220B, the prediction section 220D, the identity determination section 220C, and the image display control section 220E are provided in the image processing unit 220 of the processor 200 in the endoscope system 1, but are not necessarily provided in the processor 200. For example, an image or information may be transmitted and received by communication via the network 500 provided in a data processing device provided in another place via the network 500.

Hitherto, the endoscope system of the present invention has been described in detail, but the present invention is not limited to the above-described embodiment. As a matter of course, various improvements or modifications may be made within the scope not departing from the concept of the present invention.

The invention claimed is:
1. An endoscope system comprising:
an endoscope that captures an image of a living tissue in a body cavity; and
an image processor that performs image processing on a captured image captured by the endoscope,
wherein the endoscope includes an image sensor configured to capture an image of the living tissue, and an objective lens provided on a front side of a light receiving surface of the image sensor and configured to form the image of the living tissue on the light receiving surface, the image processor includes a three-dimensional expansion processor configured to calculate different directions of a feature part visible from at least two different capturing positions based on position information of the feature part, which is distinguishably identified from other parts and included in common in a plurality of the captured images captured at the different capturing positions by the endoscope, and to expand two-dimensional information of an image of the feature part to three-dimensional information, and an identity determination section configured to determine whether or not the feature part included in each of the plurality of images is identical using at least one of color information and an outline shape information of the feature part.

2. The endoscope system according to claim 1, wherein the capturing positions are different positions obtained by moving the endoscope with respect to the living tissue, and the three-dimensional expansion processor calculates the three-dimensional information by using the different directions of the feature part visible from the different capturing positions and distance information between the capturing positions.

3. An endoscope system comprising:

an endoscope that captures an image of a living tissue in a body cavity; and an image processor that performs image processing on a captured image captured by the endoscope, wherein the endoscope includes an image sensor configured to capture an image of the living tissue, and an objective lens provided on a front side of a light receiving surface of the image sensor and configured to simultaneously form a plurality of the images of the living tissue, obtained through a plurality of windows, on the light receiving surface as the captured image, and the image processor includes a three-dimensional expansion processor configured to calculate different directions of a feature part visible through the plurality of windows based on position information in each of images of the feature part, which is distinguishably identified from other parts and included in common in the plurality of images obtained through the plurality of windows in the captured image captured by the endoscope, and to expand two-dimensional information of the feature part to three-dimensional information, and an identity determination section configured to determine whether or not the feature part included in each of the plurality of images is identical using at least one of color information and an outline shape information of the feature part.

4. The endoscope system according to claim 3, wherein the plurality of windows include a front window facing the front side of the light receiving surface of the image sensor and a side window facing a lateral side as compared with the front window, the objective lens is configured to simultaneously form a front-view image of the living tissue obtained through the front window and a side-view image of the living tissue obtained through the side window on the light receiving surface as the captured image, and the three-dimensional expansion processor is configured to calculate different directions of the feature part visible through the front window and the side window based on position information of the feature part in the front-view image and position information of the feature part in the side-view image, the feature part being included in common in the front-view image and the side-view image in the captured image captured by the endoscope, and expand the two-dimensional information to the three-dimensional information.

5. The endoscope system according to claim 3, wherein the plurality of images include an image of an overlapping area including an identical part of the living tissue as the image, and the position information in each of the images of the feature part is information obtained when the feature part is located in the overlapping area.

6. The endoscope system according to claim 3, wherein the image sensor continuously captures images of the living tissue, and the plurality of images including the feature part are captured images having mutually different capturing positions before and after the endoscope is moved in the body cavity.

7. The endoscope system according to claim 1, wherein the three-dimensional expansion processor includes a predictive model that performs machine learning of a relationship between the two-dimensional information and the three-dimensional information using the two-dimensional information and the three-dimensional information of the image of the feature part in a plurality of the captured images including the feature part of the living tissue captured by the endoscope as training data, and is configured to acquire the three-dimensional information by inputting the two-dimensional information of the captured image captured by the endoscope to the predictive model.

* * * * *